US006752752B2

(12) United States Patent
Geitz

(10) Patent No.: US 6,752,752 B2
(45) Date of Patent: Jun. 22, 2004

(54) MULTI-SOURCE X-RAY CATHETER

(75) Inventor: Kurt Alfred Edward Geitz, Sudbury, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 13 days.

(21) Appl. No.: 10/367,559

(22) Filed: Feb. 14, 2003

(65) Prior Publication Data

US 2003/0149330 A1 Aug. 7, 2003

Related U.S. Application Data

(63) Continuation of application No. 09/709,661, filed on Nov. 10, 2000, now Pat. No. 6,554,757.

(51) Int. Cl.$^7$ ................................................. A61N 5/00
(52) U.S. Cl. .................................... 600/3; 600/3; 600/2
(58) Field of Search .............................. 600/3, 2, 1, 4, 600/5, 6, 7, 8, 101, 108, 102, 103, 104, 105, 106, 107, 114, 115, 116

(56) References Cited

U.S. PATENT DOCUMENTS

| | | | |
|---|---|---|---|
| 2,740,095 A | 3/1956 | Somes | |
| 3,248,473 A | 4/1966 | Buhmann | |
| 3,541,221 A | 11/1970 | Aupoix et al. | |
| 3,811,426 A | 5/1974 | Culver et al. | |
| 3,906,333 A | 9/1975 | Kalmanash | |
| 3,992,633 A | 11/1976 | Braun et al. | |
| 4,143,275 A | 3/1979 | Mallozzi et al. | |
| 4,323,736 A | 4/1982 | Strickland | |
| 4,459,990 A | 7/1984 | Barnea et al. | |
| 4,500,832 A | 2/1985 | Mickiewicz | |
| 4,595,843 A | 6/1986 | DelVecchio et al. | |
| 4,599,483 A | 7/1986 | Kuehn et al. | |
| 4,634,126 A | 1/1987 | Kimura | |
| 4,641,649 A | 2/1987 | Walinsky et al. | |
| 4,652,846 A | 3/1987 | Sobottka | |
| 4,810,834 A | 3/1989 | Groegl et al. | |
| 4,858,095 A | 8/1989 | Narita et al. | |
| 4,860,744 A | 8/1989 | Johnson et al. | |
| 4,993,404 A | 2/1991 | Lane | |
| 5,006,119 A | 4/1991 | Acker et al. | |
| 5,026,367 A | 6/1991 | Leckrone et al. | |
| 5,041,107 A | 8/1991 | Heil, Jr. | |
| 5,043,530 A | 8/1991 | Davies | |
| 5,084,061 A | 1/1992 | Gau et al. | |
| 5,090,043 A | 2/1992 | Parker et al. | |
| 5,127,394 A | 7/1992 | Lane | |
| 5,151,100 A | 9/1992 | Abele et al. | |
| 5,153,900 A | 10/1992 | Nomikos et al. | |
| 5,165,093 A | 11/1992 | Miller et al. | |
| 5,199,939 A | 4/1993 | Dake et al. | |
| 5,230,349 A | 7/1993 | Langberg | |
| 5,246,437 A | 9/1993 | Abela | |
| 5,253,653 A | 10/1993 | Daigle et al. | |
| 5,298,682 A | 3/1994 | Salz | |
| 5,341,281 A | 8/1994 | Skibinski | |
| 5,347,255 A | 9/1994 | Saitoh et al. | |
| 5,354,220 A | 10/1994 | Ganguly et al. | |
| 5,369,679 A | 11/1994 | Sliski et al. | |
| 5,372,603 A | 12/1994 | Acker et al. | |
| 5,379,779 A | 1/1995 | Rowland et al. | |
| 5,392,020 A | 2/1995 | Chang | |
| 5,395,362 A | 3/1995 | Sacharoff et al. | |
| 5,422,926 A | 6/1995 | Smith et al. | |
| 5,427,115 A | 6/1995 | Rowland et al. | |
| 5,442,678 A | 8/1995 | Dinsmore et al. | |
| 5,503,613 A | 4/1996 | Weinberger | |
| 5,528,652 A | 6/1996 | Smith et al. | |
| 5,542,928 A | 8/1996 | Evans et al. | |
| 5,562,633 A | 10/1996 | Wozencroft | |
| 5,566,221 A | 10/1996 | Smith et al. | |
| 5,578,008 A | 11/1996 | Hara | |
| 5,578,018 A | 11/1996 | Rowland et al. | |
| 5,591,162 A | 1/1997 | Fletcher et al. | |
| 5,593,524 A | 1/1997 | Philips | |
| 5,599,346 A | 2/1997 | Edwards et al. | |
| 5,621,780 A | 4/1997 | Smith et al. | |
| 5,651,047 A | 7/1997 | Moorman et al. | |
| 5,704,914 A | 1/1998 | Stocking et al. | |
| 5,718,688 A | 2/1998 | Wozencroft | |
| 5,720,720 A | 2/1998 | Laske et al. | |
| 5,782,740 A | 7/1998 | Schneiderman | |
| 5,793,272 A | 8/1998 | Burghartz et al. | |
| 5,795,339 A | 8/1998 | Erskine | |
| 5,816,999 A | 10/1998 | Bischoff et al. | |
| 5,865,806 A | 2/1999 | Howell | |
| 5,919,172 A | 7/1999 | Golba, Jr. | |
| 5,997,462 A | 12/1999 | Loffler | |
| 6,061,587 A | 5/2000 | Kucharczyk et al. | |
| 6,066,130 A | 5/2000 | Gregory et al. | |
| 6,095,966 A | 8/2000 | Chornenky | |
| 6,108,402 A | 8/2000 | Chornenky | |
| 6,111,933 A | 8/2000 | Schaaf et al. | |
| 6,135,997 A | 10/2000 | Laufer et al. | |
| 6,143,018 A | 11/2000 | Beuthan et al. | |
| 6,148,061 A | 11/2000 | Shefer et al. | |
| 6,171,249 B1 | 1/2001 | Chin et al. | |
| 6,183,410 B1 | 2/2001 | Jacobsen et al. | |
| 6,190,359 B1 | 2/2001 | Heruth | |
| 6,217,503 B1 | 4/2001 | Weinberg et al. | |
| 6,251,060 B1 | 6/2001 | Hooft et al. | |
| 6,296,603 B1 | 10/2001 | Turnlund et al. | |
| 6,301,328 B1 | 10/2001 | Sliski et al. | |
| 6,319,188 B1 | 11/2001 | Lovoi et al. | |
| 6,330,481 B1 | 12/2001 | Van Wijk et al. | |

(List continued on next page.)

FOREIGN PATENT DOCUMENTS

| | | |
|---|---|---|
| DE | 1 904 161 | 10/1969 |
| JP | 363291309 A | 11/1988 |
| WO | WO 97/07740 | 3/1997 |
| WO | WO 98/48899 | 11/1998 |
| WO | WO 00/09212 | 2/2000 |

Primary Examiner—Daniel Robinson
(74) Attorney, Agent, or Firm—Fulbright & Jaworski L.L.P.

(57) ABSTRACT

A multi-source x-ray/catheter delivers x-rays to a selected site within a body lumen. The x-ray sources are independently operable so that only the x-ray sources adjacent the target site generate x-rays during the procedure.

7 Claims, 2 Drawing Sheets

U.S. PATENT DOCUMENTS

| | | |
|---|---|---|
| 6,364,840 B1 | 4/2002 | Crowley |
| 6,375,651 B2 | 4/2002 | Grasso et al. |
| 6,551,278 B1 | 4/2003 | Geitz |
| 6,554,757 B1 * | 4/2003 | Geitz .................. 600/3 |
| 2001/0009970 A1 | 7/2001 | Chornenky et al. |
| 2001/0045387 A1 | 11/2001 | Amano et al. |
| 2002/0003856 A1 | 1/2002 | Gutman |

* cited by examiner

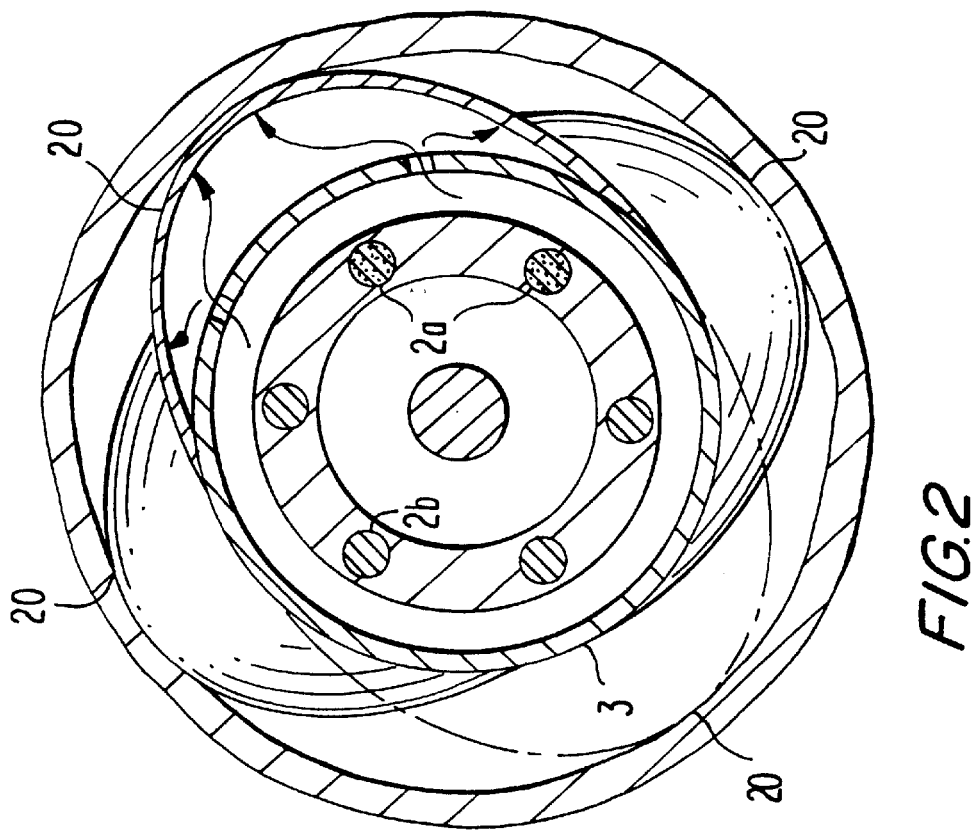
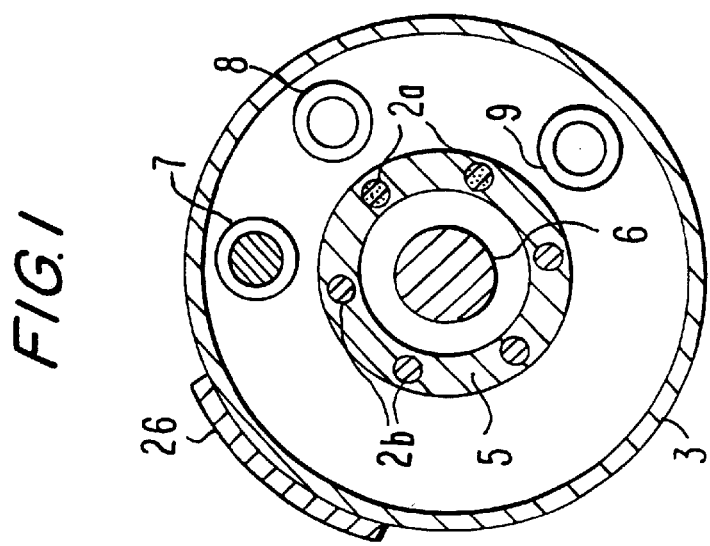

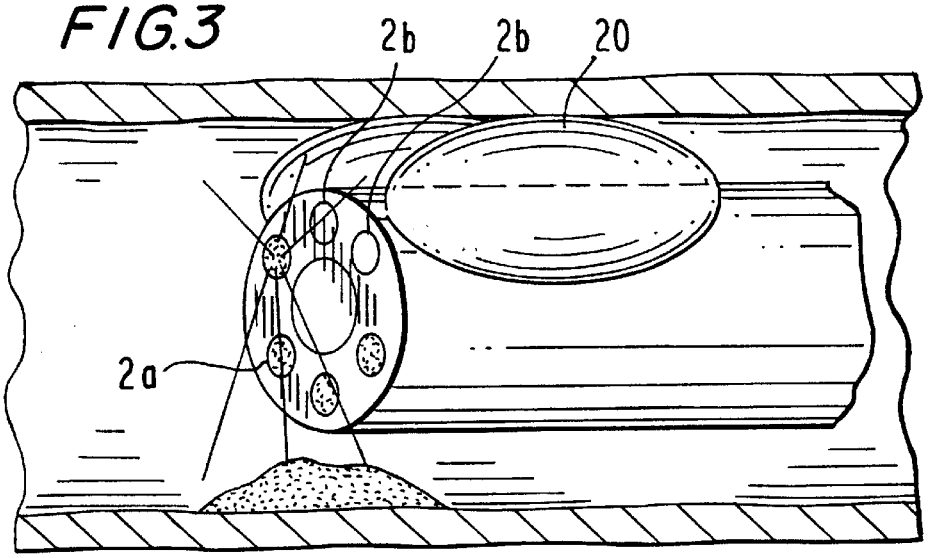
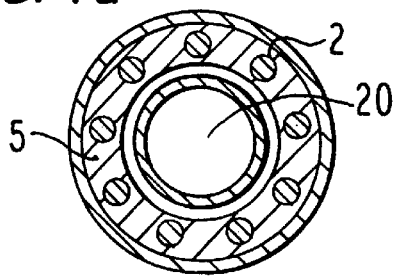
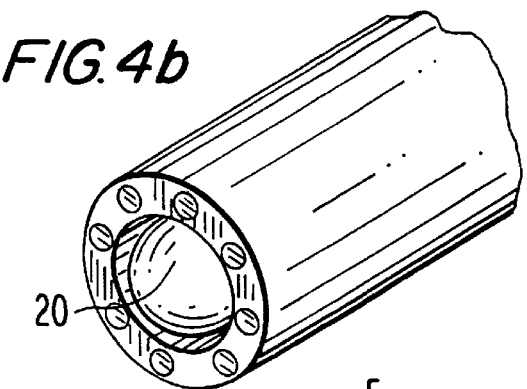
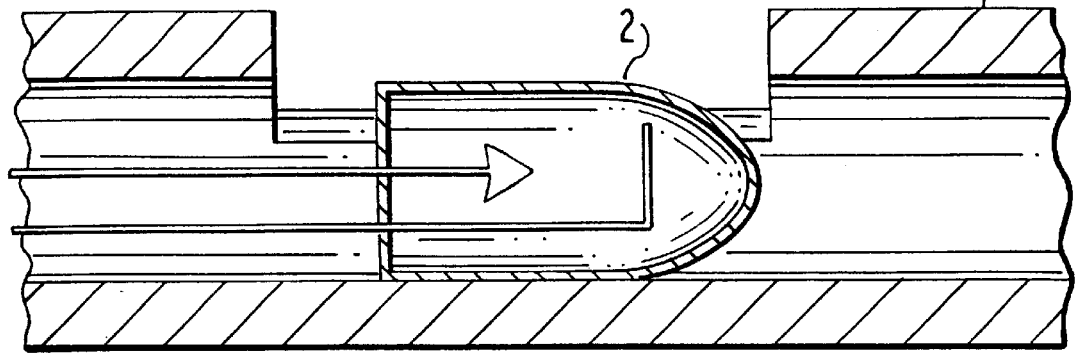

MULTI-SOURCE X-RAY CATHETER

This application is a continuation application of U.S. Ser. No. 09/709,661 filed Nov. 10, 2000 now U.S. Pat. No. 6,554,757, incorporated herein by reference.

FIELD OF THE INVENTION

The invention relates to a multi-source x-ray catheter that selectively generates x-rays to minimize adverse effects while maximizing therapeutic effectiveness.

BACKGROUND AND SUMMARY OF THE INVENTION

Traditionally, x-rays have been used in the medical industry to view bone, tissue and teeth. X-rays have also been used to treat cancerous and precancerous conditions by exposing a patient to x-rays using an external x-ray source. Treatment of cancer with x-rays presents many well documented side effects, many of which are due to the broad exposure of the patient to the therapeutic x-rays.

Minimally invasive endoscopic techniques have been developed and are used to treat a variety of conditions. Endoluminal procedures are procedures performed with an endoscope, a tubular device into the lumen of which may be inserted a variety of rigid or flexible tools to treat or diagnose a patient's condition.

The desire for improved minimally invasive medical devices and techniques have led to the development of miniaturized x-ray devices that may be used in the treatment or prevention of a variety of medical conditions. International Publication No. WO 98/48899 discloses a miniature x-ray unit having an anode and cathode separated by a vacuum gap positioned inside a metal housing. The anode includes a base portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 discloses an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

Miniaturized x-rays are not foolproof, however, and present difficulties. The x-ray unit generates heat, which can damage adjacent tissue. Additionally, x-rays are not localized and irradiate local tissue rather than only irradiating the desired site. Also, it is difficult to maintain the positioning of these instruments inside at the desired location. Improved miniaturized x-ray units the overcome these difficulties are desirable.

Other techniques are used to treat tumors with x-rays, including planting a seed of radioactive material at the tumor site, typically accomplished with endoluminal procedures. However, the patient becomes "hot", i.e., radioactive, and the procedure risks exposure of the medical personnel to radiation exposure.

As noted above, many types of cancerous and precancerous conditions are treated by irradiating the tumor or site with x-rays. However, the x-rays are broadcast over a large area of healthy tissue in addition to the tumor, since the radiation is administered from outside the body so that it penetrates the skin and any internal organs or tissue to reach the desired site. To avoid this, miniaturized x-ray systems which generate x-rays at the desired site are a desirable alternative to conventional apparatus.

Many types of cancer occur in a body cavity or lumen, such as in the rectum, vagina, esophagus or pulmonary passages. It is desirable to treat these cancers using miniaturized x-ray sources in combination with endoscopic techniques, which are minimally invasive to the patient, so that the cancer or other intraluminal tissue is directly treated with x-rays.

The present invention overcomes the difficulties associated with x-ray therapy and apparatus of the prior art by providing an multi-source x-ray device that generates x-rays at the site of treatment and minimizes exposure of other tissues to irradiation.

BRIEF DESCRIPTION OF THE DRAWINGS

FIG. 1 is a cross-section of a preferred embodiment of a multi-source x-ray catheter according to the invention.

FIG. 2 is an alternative embodiment of multi-source x-ray catheter of the invention;

FIG. 3 is a cut-away view of a multi-source x-ray catheter of the present invention inside a body lumens;

FIGS. 4a and 4b are an alternative embodiment having a hollow central lumen with a balloon therein which inflates to push the x-ray sources towards the desired site; and FIG. 5 is a detail of an x-ray source according to the invention.

DETAILED DESCRIPTION

FIG. 1 is a cross section of a preferred multi-source x-ray catheter according to the invention. Catheter 1 includes at least two x-ray sources connected to a power supply by, e.g., a coaxial cable. The power supply delivers sufficient energy to the x-ray source 2 to generate therapeutically effective x-rays. Typically, voltages of from 10 to 60 kilovolts (kV) are needed to generate the x-rays. X-ray sources 2 are located inside a lumen of x-ray shield 5 which is impenetrable to x-rays except at its distal end or, optionally, via transparent windows. The x-ray sources are preferably evenly spaced about a circular catheter body and are preferably independently operable, that is, they may be selectively turned on or off by the operator (see 2a and 2b). The x-ray sources range from 1 to 15 mm in length and width. The overall diameter of the device ranges from 10 to 100 mm.

Inner guide 6 is located in the center lumen of catheter 1 and is surrounded by x-ray shields. Additional lumens in the catheter may contain a guide wire 7, circulation means 8, visual equipment 9, or other endoscopic tools as desired.

A preferred embodiment, shown in FIGS. 2 and 3 includes at least one inflatable positioning balloon 20 adhered to the outer wall of the x-ray tube. Positioning balloon 20 is inflated after proper positioning of the apparatus in the body lumen so that the position of the x-ray source is maintained throughout treatment. Positioning balloon 20 may be adhered to the exterior wall of the x-ray tube by a suitable adhesive and is designed to bit inside catheter shields. This embodiment shows x-ray sources in the on 2a and off 2b positions. It is preferred that a plurality of balloons are provided. Alternatively, a multi-chambered balloon is provided to aid proper positioning of the apparatus in the body lumen.

In a particularly preferred embodiment, a gas or liquid coolant is passed through balloon 20 via tubes which communicate with both the interior of positioning balloon 20 and a gas or liquid reservoir. A respective circulation duct is provided for each balloon or balloon chamber so that they may be independently inflated. The positioning balloons 20 may be inflated with a gas or a liquid, but an x-ray absorbent liquid is preferred. Normal saline is a particularly preferred liquid because it has a high heat capacity, is x-ray absorbent, and, in the unlikely event of leakage, is compatible with the patient.

Optionally, a balloon 20 may be positioned in the center of the device as shown in FIG. 4 and inflated to push x-ray sources 2 outwardly in the direction of the target tissue. In this embodiment, catheter body 1 and x-ray shield are made of flexible material, e.g., plastic, to expand or contract with the inflation or deflation of the balloon.

Thermocouple 26 may be optionally affixed or placed in the vicinity of the x-ray source to measure temperature during the procedure. Thermocouple 26 may be in the form of a bimetallic strip and is operatively connected to a temperature display device so that the temperature is monitored during the procedure.

FIG. 3 shows an endoscope having an x-ray catheter according to the invention positioned inside a body lumen. The device is positioned inside the lumen, and balloons 20 are inflated to position the catheter near the target site, in this case, a tumor. The x-ray sources 2a adjacent to the tumor are turned on by the operator to generate x-rays, while the x-ray sources opposite the tumor remain in the off position 2b. The tumor is irradiated with the appropriate dose of x-rays, and withdrawn from the body lumen.

FIG. 5 is a cutaway view of a typical x-ray source used in accordance with the invention.

The present invention also relates to methods of treatment, prophylaxis and adjunctive therapy using the miniaturized x-ray apparatus of the present invention. Suitable for use with other endoscopic equipment, the x-ray device may be used to treat cancers of bodily lumens such as colorectal cancer, vaginal cancer, esophageal cancer, pulmonary cancers such as lung cancers, stomach cancer, oral cancers, or any cancer accessible by a bodily lumen by positioning the device adjacent the target tissue and irradiating the tissue with a therapeutically effective amount of x-rays. In similar fashion, one can treat pre-cancerous conditions or conditions related with cancer such as gastroesophageal reflux disease (GERD).

Although the present invention has been shown and described with respect to several preferred embodiments thereof, additional embodiments will be apparent to the skilled artisan without departing from the spirit and scope of the invention.

What is claimed is:

1. An apparatus for delivering x-rays to a selected site within a body cavity comprising:
   an endoscope having a central lumen;
   an x-ray shield which is impenetrable to x-rays positioned in said central lumen, said x-ray shield being penetrable to x-rays at a distal end thereof;
   at least two x-ray sources positioned in respective lumens of said x-ray shield, said x-ray sources being operably connected to a power source and a multi-chambered positioning balloon on an outer surface of said endoscope.

2. The apparatus of claim 1, further comprising a plurality of inflatable positioning balloons on the outer surface of said endoscope.

3. The apparatus of claim 1, wherein said endoscope has a visual lumen containing a visual device therein.

4. The apparatus of claim 1, further comprising a thermocouple affixed to the apparatus in the vicinity of the x-ray source.

5. A method of treating a cancerous or precancerous condition in a lumen of a patient comprising:
   inserting the apparatus of claim 1 into the lumen or a patient having a cancerous or precancerous condition in a body lumen;
   positioning the apparatus proximate such that said at least two x-ray sources are proximate to the cancerous or precancerous condition; and
   irradiating the tumor with a therapeutically effective amount of x-ray radiation generated from at least one of the x-ray sources.

6. A method of treating a cancerous or precancerous tissue in a lumen of a patient comprising:
   inserting the apparatus of claim 1 into the lumen of a patient having a cancerous or precancerous tumor in a lumen;
   positioning the apparatus proximate such that said at least two x-ray sources are proximate to the cancerous or precancerous tumor; and
   irradiating the tumor with a therapeutically effective amount of x-ray radiation generated from at least one of the x-ray sources.

7. A method of treating a cancerous or precancerous tumor in a lumen of a patient comprising:
   inserting the apparatus of claim 1 into the lumen of a patient having a cancerous or precancerous tumor in a lumen;
   positioning the apparatus proximate such that said x-ray sources are proximate to the cancerous or precancerous tumor; and
   irradiating the tumor with a therapeutically effective amount of x-ray radiation generated from at least one of the x-ray sources.

* * * * *